(12) United States Patent
Roberts et al.

(10) Patent No.: US 7,052,689 B2
(45) Date of Patent: *May 30, 2006

(54) METHOD FOR PRODUCING THERAPEUTICALLY SUITABLE GLUTAMINASE

(75) Inventors: Joseph Roberts, 6 Sunturf Cir., Columbia, SC (US) 29223; Thomas W MacAllister, Columbia, SC (US); Natarajan Sethuraman, Columbia, SC (US); Abbie G. Freeman, Columbia, SC (US)

(73) Assignees: ME Medical Enzymes AG, Berlin (DE); Joseph Roberts, Columbia, SC (US)

(*) Notice: Subject to any disclaimer, the term of this patent is extended or adjusted under 35 U.S.C. 154(b) by 640 days.

This patent is subject to a terminal disclaimer.

(21) Appl. No.: 09/842,628

(22) Filed: Apr. 27, 2001

(65) Prior Publication Data

US 2002/0064862 A1    May 30, 2002

Related U.S. Application Data

(62) Division of application No. 08/050,482, filed as application No. PCT/US92/10421 on Dec. 4, 1992, now Pat. No. 6,312,939.

(30) Foreign Application Priority Data

Dec. 4, 1991   (DE) .............................. P 4140003.8

(51) Int. Cl.
    *A01N 63/00*   (2006.01)
    *A61K 38/46*   (2006.01)
    *A61K 39/108*  (2006.01)
    *C07H 21/04*   (2006.01)
    *C12P 21/06*   (2006.01)

(52) U.S. Cl. ............... 424/93.47; 424/94.6; 424/260.1; 424/201.1; 536/23.7; 435/69.1

(58) Field of Classification Search ............... 424/93.4; 435/170, 253.3
See application file for complete search history.

(56) References Cited

U.S. PATENT DOCUMENTS 4,560,661 A * 12/1985 Katsumata et al. ......... 435/183
4,762,707 A    8/1988 Jansen et al.
5,232,840 A *  8/1993 Olins ........................ 435/69.1

FOREIGN PATENT DOCUMENTS

CA        1 168 150       5/1984
JP        01300889 A2 * 12/1989

OTHER PUBLICATIONS

Davidson L. "Purification and Properties of an L-Glutaminase-L-Asparaginase from *Pseudomonas acidovorans*" Journal of Bacteriology (Mar. 1997) pp. 1379-1386.*

Roberts, J. "Purification and Properties of a Highly Antitumor Glutaminase-Aspariginase from Pseudomonas 7A" Journ Bio Chem (Apr. 1976) vol. 251, No. 7 pp. 2119-2123).*

Smith, E.M. "Molecular Cloning of a cDNA for Rat Hepatic Glutaminase" J Biol Chem vol. 286, No. 18 pp. 10601-10636.*

Shapiro, R.A. "Isolation, Characterization, and in Vitro Expression of a cDNA That Encodes the Kidney Isoenzyme of the Mitochondrial Glutaminase" Journ Biol Chem (Oct. 1991) vol. 266, pp. 18792-18796.*

Tanaka, S., et al., "Structures of Amidohydrolases: .Amino Acid Sequence of a Glutaminase-Asparaginase from *Acinetobacter Glutaminasificans* and Preliminary Crystallographic Data for an Asparaginase from *Erwinia Chrysanthemi*," *The Journal of Biological Chemistry*, vol. 363, No. 18, Jun. 25, 1988, pp. 8583-8591.

Lubkowski, J., et al., "Structure Characterization of Pseudomonas 7A Glutaminase-Asparaginase", *Biochemistry*, Abstract, Aug. 30, 1994, vol. 33, No. 34, pp. 10257-10265.

Ammon, H., et al., "Preliminary Crystal Structure of *Acinetobacter Glutaminasificans* Glutaminase-Asparaginase," *The Journal of Biological Chemistry*, vol. 263, No. 1, Jan. 5, 1988, pp. 150-156.

Wlodawer, A., et al., "Characterization of Crystals of L-Glutaminase-Asparaginase from Acinetobacter Glutaminasificans and Pseudomonas 7A," *J. Mol. Biol.*, Abstract, May 25, 1977, vol. 112, No. 3, pp. 515-519.

Roberts, J., et al., "Isolation, Cryatallization, and Properties of *Achromobacteraceae* Glutaminase-Asparaginase with Antitumor Activity," *The Journal of Biological Chemistry*, vol. 247, No. 1, Jan. 10, 1972, pp. 84-90.

UniProtKB/Swiss-Prot Entry P10182.

Minton et al., "Nucleotide Sequence Of The Erwinia Chrysanthemi NCPPB 1066 L-Asparaginase Gene", *Gene*, vol. 46:25-35, (1986).

(Continued)

*Primary Examiner*—James Housel
*Assistant Examiner*—Tim Brown
(74) *Attorney, Agent, or Firm*—Foley & Lardner LLP

(57) ABSTRACT

DNA encoding a therapeutically suitable glutaminase has been molecularly cloned. This allows one to obtain a polypeptide which is a therapeutically suitable glutaminase free of contaminating endotoxin. It has been found that this polypeptide is a potent anti-viral agent and when coupled to an anti-tumor monoclonal antibody is a potent anticancer agent. The glutaminase of the present invention is particularly useful for treating lung, breast and colon cancer cells and in the treatment of HIV-infected cells.

6 Claims, 10 Drawing Sheets

OTHER PUBLICATIONS

Kim et al., "Asparaginase II *Saccharomyces Cerevisiae*", *J. Biol. Chem.*, vol. 263:11948-11953, (1988).

Ovejera et al., "Efficacy Of 6-Diazo-5-oxo-L-Norteucine and N-[-N-γ-Glutamyl-6-Diazo-5-oxo-Norleucinyl]-6-diazo-5-oxo-Norleucine Against Experimental Tumors In Convenrtional And Nude Mice", *Cancer Research*, vol. 39:3220-3324, (1979).

Houchens, et al., "Therapy For Mouse Tumors And Human Xenografts With The Antitumor Antibiotic AT-125", *Cancer Treatment Reports*, vol. 63:473-476, (1979).

Duvall, "6-Diazo-5-oxo-L-Norleucine", *Cancer Chemother. Reports*, vol. 7:86-98, (1960).

Roberts, "Purification And Properties Of A Highly Potent Antitumor Glutaminase-Asparaginase From Pseudomonas 7A", *J. Biol. Chem.*, vol. 251:2119-2123, (1976).

Holcenberg et al., "Physical Properties Of Antitumor Glutaminase-Asparaginase From Pseudomonas 7A", *J. Biol. Chem.*, vol. 251:5375-5380, (1976).

Roberts, et al., "Biologic And Antineoplastic Effects Of Enzyme-Mediated In Vivo Depletion Of L-Glutamine, L-Tryptophan, And L-Histidine", *Cancer Treatment Reports*, vol. 63:1045-1054, (1979).

Roberts, et al., Inhibition Of Mouse Retroviral Disease By Bioactive Glutaminase-Asparaginase, *J. Gen. Virol.*, vol. 72:299-305, (1991).

Bonthron, "L-Asparaginase II Of *Escherichia Coli* K-12: Cloning, Mapping And Sequencing Of The ansB Gene", *Gene*, vol. 91:101-105, (1990).

Nicolau, et al., "Liposomes As Carriers For In Vivo Gene Transfer And Expression", *Meth. Enzymol.*, vol. 149:157-176, (1987).

Holcenberg et al., *Biochemistry*, vol. 17(3):411-417, (1978).

Wu, et al., "Receptor-Mediated Gene Delivery In Vivo", *J. Biol. Chem.*, vol. 266:14338-14342, (1991).

Schmer, et al., "Kinetics Of Uptake And Activity in Mouse Liver Of Glutaminse Coupled To Desialated Orosomucoid", *Biochimica et Biophysica Acta*, vol. 538:397-405, (1978).

Ollenschlaeger, et al., "Intestinal Glutamine Metabolism Of Patients With HIV-Infection", *Clinical Nutrition*, vol. 9:48-49, (1990).

Roberts, et al., "Glutaminase Has Potent Antiretroviral Activity In Vivo", Abstract, *Proc. Am. Assoc. Cancer Res.*, vol. 30:454, (1989).

Shapiro, et al., "Isolation, Characterization, And In Vitro Expression Of A cDNA That Encodes The Kidney Isoenzyme Of The Mitochondiral Glutaminase", *J. Biol. Chem.*, vol. 266:18792-18796, (1991).

Katunuma, et al., "Organ Specific Control Of Glutamine Metabolism", *Adv. Enz. Reg.*, vol. 5:55-69, (1967).

Goldstein, "Relation Of Glutamate To Ammonia Productio nin The Rat Kidney", *Am. J. Physiol.*, vol. 210:661-666, (1966).

Curthoys, et al., "The Distribution Of Glutaminase Isoenzymes In The Various Structures Of The nephron In Normal, Acidotic, And Alkatotic Rat Kidney", *J. Biol. Chem.*, vol. 248:162-168, (1973).

Goldstein, "Relation Of Glutamate To Ammonia Pruductio nin The Rat Kidney", pp. 661-666.

Smith, Molecular Cloning Of A cDNA For Rat Hepatic Glutaminase, pp. 10631-10636, (1980).

Smith, "Rat Hepatic Glutaminase: Purification And Immunochemical Characterization", pp. 740-751, (1987).

Banner, "Isolation Of A cDNA For Rat Brain Glutaminase", pp. 247-254, (1988).

* cited by examiner

FIG. 1A

| AAG | GAA | GTG | GAG | AAC | CAG | CAG | AAG | CTG | GCC | AAC | GTG | GTG | ATC | CTG | GCC | 48 |
|---|---|---|---|---|---|---|---|---|---|---|---|---|---|---|---|---|
| Lys | Glu | Val | Glu | Asn | Gln | Gln | Lys | Leu | Ala | Asn | Val | Val | Ile | Leu | Ala | |
| 1 | | | | 5 | | | | | 10 | | | | | 15 | | |

| ACC | GGC | ACC | ATC | GCC | GGC | GCT | GGC | GCC | AGC | AAC | AGC | GCC | | | | 96 |
|---|---|---|---|---|---|---|---|---|---|---|---|---|---|---|---|---|
| Thr | Gly | Thr | Ile | Ala | Gly | Ala | Gly | Ala | Ser | Asn | Ser | Ala | | | | |
| | | 20 | | | | | 25 | | | | | 30 | | | | |

| ACC | TAC | CAG | GCT | GCC | AAG | GTT | GGC | GAC | AAG | CTG | ATT | GCC | GGC | GTG | 144 | |
|---|---|---|---|---|---|---|---|---|---|---|---|---|---|---|---|---|
| Thr | Tyr | Gln | Ala | Ala | Lys | Val | Gly | Asp | Lys | Leu | Ile | Ala | Gly | Val | | |
| | | 35 | | | | | 40 | | | | | 45 | | | | |

| CCG | GAG | CTG | GCC | GAC | AAT | GTG | CGC | GGC | GAG | CAG | GTG | ATG | CAG | | | 192 |
|---|---|---|---|---|---|---|---|---|---|---|---|---|---|---|---|---|
| Pro | Glu | Leu | Ala | Asp | Asn | Val | Arg | Gly | Glu | Gln | Val | Met | Gln | | | |
| 50 | | | | | 55 | | | | | 60 | | | | | | |

| ATC | GCC | TCC | GAA | AGC | ATC | ACC | AAC | GAC | GAC | CTC | AAG | CTG | GCA | AGC | 240 | |
|---|---|---|---|---|---|---|---|---|---|---|---|---|---|---|---|---|
| Ile | Ala | Ser | Glu | Ser | Ile | Thr | Asn | Asp | Asp | Leu | Lys | Leu | Ala | Ser | | |
| 65 | | | | | 70 | | | | | 75 | | | | | 80 | |

FIG. 1B

```
AGC GTG GCC GAG CTG GCC GAC AGC AAT GAC GTC GAT GGC ATC GTC ATC  288
Ser Val Ala Glu Leu Ala Asp Ser Asn Asp Val Asp Gly Ile Val Ile
                 85                  90                  95

ACC CAT GGC ACC GAC ACC CTG GAA GAA ACC GCC TAC TTT TTG AAC CTC  336
Thr His Gly Thr Asp Thr Leu Glu Glu Thr Ala Tyr Phe Leu Asn Leu
            100                 105                 110

GTG GAA AAG ACC GAC AAG CCG ATC GTC GTG GTC GGT TCC ATG CGC CCC  384
Val Glu Lys Thr Asp Lys Pro Ile Val Val Gly Ser Met Arg Pro
        115                 120                 125

GGC ACC GCC ATG TCC GAC GGC ATG CTC AAC CTG TAC AAC GCC GTG  432
Gly Thr Ala Met Ser Asp Gly Met Leu Asn Leu Tyr Asn Ala Val
    130                 135                 140

GCC GTG GCC AGC AAC AAG GAC TCG CGC GGC AAG GGC GTG CTG GTG ACC  480
Ala Val Ala Ser Asn Lys Asp Ser Arg Gly Lys Gly Val Leu Val Thr
145                 150                 155                 160
```

FIG. IC

```
ATG AAC GAC GAG ATC CAG TCC GGG CGT GAC GTG AGC AAG TCG ATC AAC   528
Met Asn Asp Glu Ile Gln Ser Gly Arg Asp Val Ser Lys Ser Ile Asn
                165                 170                 175

ATC AAG ACC GAA GCC TTC AAG AGC GCC TGG GGC CCG CTG GGC ATG GTG   576
Ile Lys Thr Glu Ala Phe Lys Ser Ala Trp Gly Pro Leu Gly Met Val
            180                 185                 190

GTG GAA GGC AAG TCG TAC TGG TTC CGC CTG CCG GCC AAG CGC CAC ACG   624
Val Glu Gly Lys Ser Tyr Trp Phe Arg Leu Pro Ala Lys Arg His Thr
        195                 200                 205

GTC AAC TCC GAG TTC GAC ATC AGC AAG CAG ATC AGC AGC CTG CCC CAG GTG   672
Val Asn Ser Glu Phe Asp Ile Ser Lys Gln Ile Ser Ser Leu Pro Gln Val
    210                 215                 220

GAC ATC GCC TAC AGC TAT GGC AAC GTC ACC GAC ACG GCC TAC AAG GCC   720
Asp Ile Ala Tyr Ser Tyr Gly Asn Val Thr Asp Thr Ala Tyr Lys Ala
225                 230                 235                 240

CTG GCA CAG AAC GGC GCC AAG GCG CTG ATC CAT GCC GGC ACC GGC AAT   768
Leu Ala Gln Asn Gly Ala Lys Ala Leu Ile His Ala Gly Thr Gly Asn
            245                 250                 255
```

FIG. ID

```
GGC TCG GTG TCG TCG CGG GTG GTG CCA GCC CTG CAG GAG CTG CGC AAG 816
Gly Ser Val Ser Ser Arg Val Val Pro Ala Leu Gln Glu Leu Arg Lys
        260                 265                 270

AAC GGC GTG CAG ATC ATT CGT TCG TCA CGT CAA CAG GGC GGT TTC GTG 864
Asn Gly Val Gln Ile Ile Arg Ser Ser Arg Gln Gln Gly Gly Phe Val
        275                 280                 285

CTG CGT AAC GCC GAG CAG CCC GAC AAG AAC GAC TGG GTC GTG GCC 912
Leu Arg Asn Ala Glu Gln Pro Asp Lys Asn Asp Trp Val Val Ala
    290                 295                 300

CAC GAC CTG AAC CCG CAG AAG GCC CGC ATC CTG GCG ATG GTG GCA ATG 960
His Asp Leu Asn Pro Gln Lys Ala Arg Ile Leu Ala Met Val Ala Met
        305                 310                 315                 320

ACC AAG ACC CAG GAC AGC GAC AGC CTG CAG CGC ATT TTC TGG GAA TAC 1008
Thr Lys Thr Gln Asp Ser Asp Ser Leu Gln Arg Ile Phe Trp Glu Tyr
        325                 330                 335

TGATAA 1014
```

| Primer | Sequence (5'–3') | Coordinates |
|---|---|---|
| JR-1 | TGCAGCTTGAGCAGGTCGTC | 237 - 217 |
| JR-2 | CTGGCCGACCTGGCCAATGTG | 151 - 171 |
| AF-1 | CCTACTTTTGAACCTCGTG | 320 - 339 |
| AF-2 | CAAGTCGTACTGGTTCCGCC | 585 - 604 |
| AF-3 | CAATCGTCCTGGGCGACTCGTG | 1250 - 1230 |
| AF-4 | GCAGATCATTCGTTCGTCCA | 825 - 843 |
| AF-5 | TGACGATGCCATCGACGTCA | 286 - 267 |
| AF-6 | TCACGTCACGCCCGGACTGG | 514 - 495 |
| AF-7 | AGCTCCTGCAGGGCTGGCAC | 809 - 790 |

SEQUENCE LISTING

```
<160> NUMBER OF SEQ ID NOS: 22

<210> SEQ ID NO 1
<211> LENGTH: 1014
<212> TYPE: DNA
<213> ORGANISM: Pseudomonas sp.
<220> FEATURE:
<221> NAME/KEY: CDS
<222> LOCATION: (1)..(1008)
```

```
<400> SEQUENCE: 1 aag gaa gtg gag aac cag cag aag ctg gcc aac gtg gtg atc ctg gcc      48
Lys Glu Val Glu Asn Gln Gln Lys Leu Ala Asn Val Val Ile Leu Ala
  1               5                  10                  15 acc ggc ggc acc atc gcc ggc gct ggc gcc agc gcg gcc aac agc gcc      96
Thr Gly Gly Thr Ile Ala Gly Ala Gly Ala Ser Ala Ala Asn Ser Ala
             20                  25                  30 acc tac cag gct gcc aag gtt ggc gtc gac aag ctg att gcc ggc gtg     144
Thr Tyr Gln Ala Ala Lys Val Gly Val Asp Lys Leu Ile Ala Gly Val
         35                  40                  45 ccg gag ctg gcc gac ctg gcc aat gtg cgc ggc gag cag gtg atg cag     192
Pro Glu Leu Ala Asp Leu Ala Asn Val Arg Gly Glu Gln Val Met Gln
 50                  55                  60 atc gcc tcc gaa agc atc acc aac gac gac ctg ctc aag ctg gca agc     240
Ile Ala Ser Glu Ser Ile Thr Asn Asp Asp Leu Leu Lys Leu Ala Ser
 65                  70                  75                  80 agc gtg gcc gag ctg gcc gac agc aat gac gtc gat ggc atc gtc atc     288
Ser Val Ala Glu Leu Ala Asp Ser Asn Asp Val Asp Gly Ile Val Ile
                 85                  90                  95 acc cat ggc acc gac acc ctg gaa gaa acc gcc tac ttt ttg aac ctc     336
Thr His Gly Thr Asp Thr Leu Glu Glu Thr Ala Tyr Phe Leu Asn Leu
            100                 105                 110 gtg gaa aag acc gac aag ccg atc gtc gtg gtc ggt tcc atg cgc ccc     384
Val Glu Lys Thr Asp Lys Pro Ile Val Val Val Gly Ser Met Arg Pro
        115                 120                 125 ggc acc gcc atg tcc gcc gac ggc atg ctc aac ctg tac aac gcc gtg     432
Gly Thr Ala Met Ser Ala Asp Gly Met Leu Asn Leu Tyr Asn Ala Val
130                 135                 140 gcc gtg gcc agc aac aag gac tcg cgc ggc aag ggc gtg ctg gtg acc     480
Ala Val Ala Ser Asn Lys Asp Ser Arg Gly Lys Gly Val Leu Val Thr
145                 150                 155                 160 atg aac gac gag atc cag tcc ggg cgt gac gtg agc aag tcg atc aac     528
Met Asn Asp Glu Ile Gln Ser Gly Arg Asp Val Ser Lys Ser Ile Asn
                165                 170                 175 atc aag acc gaa gcc ttc aag agc gcc tgg ggc ccg ctg ggc atg gtg     576
Ile Lys Thr Glu Ala Phe Lys Ser Ala Trp Gly Pro Leu Gly Met Val
            180                 185                 190 gtg gaa ggc aag tcg tac tgg ttc cgc ctg ccg gcc aag cgc cac acg     624
Val Glu Gly Lys Ser Tyr Trp Phe Arg Leu Pro Ala Lys Arg His Thr
        195                 200                 205 gtc aac tcc gag ttc gac atc aag cag atc agc agc ctg ccc cag gtg     672
Val Asn Ser Glu Phe Asp Ile Lys Gln Ile Ser Ser Leu Pro Gln Val
    210                 215                 220 gac atc gcc tac agc tat ggc aac gtc acc gac acg gcc tac aag gcc     720
Asp Ile Ala Tyr Ser Tyr Gly Asn Val Thr Asp Thr Ala Tyr Lys Ala
225                 230                 235                 240 ctg gca cag aac ggc gcc aag gcg ctg atc cat gcc ggc acc ggc aat     768
Leu Ala Gln Asn Gly Ala Lys Ala Leu Ile His Ala Gly Thr Gly Asn
                245                 250                 255 ggc tcg gtg tcg tcg cgg gtg gtg cca gcc ctg cag gag ctg cgc aag     816
Gly Ser Val Ser Ser Arg Val Val Pro Ala Leu Gln Glu Leu Arg Lys
            260                 265                 270 aac ggc gtg cag atc att cgt tcg tca cgt caa cag ggc ggt ttc gtg     864
Asn Gly Val Gln Ile Ile Arg Ser Ser Arg Gln Gln Gly Gly Phe Val
        275                 280                 285 ctg cgt aac gcc gag cag ccc gac gac aag aac gac tgg gtc gtg gcc     912
Leu Arg Asn Ala Glu Gln Pro Asp Asp Lys Asn Asp Trp Val Val Ala
    290                 295                 300 cac gac ctg aac ccg cag aag gcc cgc atc ctg gcg atg gtg gca atg     960
His Asp Leu Asn Pro Gln Lys Ala Arg Ile Leu Ala Met Val Ala Met
```

-continued

```
His Asp Leu Asn Pro Gln Lys Ala Arg Ile Leu Ala Met Val Ala Met
305                 310                 315                 320 acc aag acc cag gac agc aag gag ctg cag cgc att ttc tgg gaa tac     1008
Thr Lys Thr Gln Asp Ser Lys Glu Leu Gln Arg Ile Phe Trp Glu Tyr
                325                 330                 335 tgataa                                                              1014
```

<210> SEQ ID NO 2
<211> LENGTH: 336
<212> TYPE: PRT
<213> ORGANISM: Pseudomonas sp.

<400> SEQUENCE: 2

```
Lys Glu Val Glu Asn Gln Gln Lys Leu Ala Asn Val Val Ile Leu Ala
1               5                   10                  15

Thr Gly Gly Thr Ile Ala Gly Ala Gly Ala Ser Ala Ala Asn Ser Ala
                20                  25                  30

Thr Tyr Gln Ala Ala Lys Val Gly Val Asp Lys Leu Ile Ala Gly Val
            35                  40                  45

Pro Glu Leu Ala Asp Leu Ala Asn Val Arg Gly Glu Gln Val Met Gln
    50                  55                  60

Ile Ala Ser Glu Ser Ile Thr Asn Asp Asp Leu Leu Lys Leu Ala Ser
65                  70                  75                  80

Ser Val Ala Glu Leu Ala Asp Ser Asn Asp Val Asp Gly Ile Val Ile
                85                  90                  95

Thr His Gly Thr Asp Thr Leu Glu Glu Thr Ala Tyr Phe Leu Asn Leu
            100                 105                 110

Val Glu Lys Thr Asp Lys Pro Ile Val Val Gly Ser Met Arg Pro
    115                 120                 125

Gly Thr Ala Met Ser Ala Asp Gly Met Leu Asn Leu Tyr Asn Ala Val
130                 135                 140

Ala Val Ala Ser Asn Lys Asp Ser Arg Gly Lys Gly Val Leu Val Thr
145                 150                 155                 160

Met Asn Asp Glu Ile Gln Ser Gly Arg Asp Val Ser Lys Ser Ile Asn
                165                 170                 175

Ile Lys Thr Glu Ala Phe Lys Ser Ala Trp Gly Pro Leu Gly Met Val
            180                 185                 190

Val Glu Gly Lys Ser Tyr Trp Phe Arg Leu Pro Ala Lys Arg His Thr
    195                 200                 205

Val Asn Ser Glu Phe Asp Ile Lys Gln Ile Ser Ser Leu Pro Gln Val
210                 215                 220

Asp Ile Ala Tyr Ser Tyr Gly Asn Val Thr Asp Thr Ala Tyr Lys Ala
225                 230                 235                 240

Leu Ala Gln Asn Gly Ala Lys Ala Leu Ile His Ala Gly Thr Gly Asn
                245                 250                 255

Gly Ser Val Ser Ser Arg Val Pro Ala Leu Gln Glu Leu Arg Lys
            260                 265                 270

Asn Gly Val Gln Ile Ile Arg Ser Ser Arg Gln Gln Gly Gly Phe Val
    275                 280                 285

Leu Arg Asn Ala Glu Gln Pro Asp Asp Lys Asn Asp Trp Val Val Ala
290                 295                 300

His Asp Leu Asn Pro Gln Lys Ala Arg Ile Leu Ala Met Val Ala Met
305                 310                 315                 320

Thr Lys Thr Gln Asp Ser Lys Glu Leu Gln Arg Ile Phe Trp Glu Tyr
                325                 330                 335
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
tgcagcttga gcaggtcgtc                                           20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 4
ctggccgacc tggccaatgt g                                         21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
cctacttttt gaacctcgtg                                           20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
caagtcgtac tggttccgcc                                           20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 7
caatcgtcct ggcgactcgt g                                         21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
gcagatcatt cgttcgtcca                                           20

<210> SEQ ID NO 9
<211> LENGTH: 20
<212> TYPE: DNA
<213> ORGANISM: Artificial Sequence
<220> FEATURE:

<223> OTHER INFORMATION: Description of Artificial Sequence: Primer

<400> SEQUENCE: 9
tgacgatgcc atcgacgtca                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
tcacgtcacg cccggactgg                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
agctcctgca gggctggcac                                              20

<210> SEQ ID NO 12
<211> LENGTH: 14
<212> TYPE: DNA
<213> ORGANISM: Artificial Sequence
<220> FEATURE:
<223> OTHER INFORMATION: Description of Artificial Sequence: Probe
<221> NAME/KEY: modified_base
<222> LOCATION: (9)
<223> OTHER INFORMATION: a, t, c, g, other or unknown

<400> SEQUENCE: 12
aargargtng araa                                                    14

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Probe

<400> SEQUENCE: 13
atggaygayg arathgar                                                18

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Probe

<400> SEQUENCE: 14
athttytggg arta                                                    14

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 15

```
gccggatcca tatgaaggaa gtggagaacc agcag                          35
```

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 16

```
gcgcggatcc gtcgacgcca accttggcag                                30
```

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: CDS
<222> LOCATION: (9)..(26)

<400> SEQUENCE: 17

```
ggatccat atg aag gaa gtg gag aac                                26
        Met Lys Glu Val Glu Asn
          1               5
```

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Met Lys Glu Val Glu Asn
  1               5
```

<210> SEQ ID NO 19
<211> LENGTH: 91
<212> TYPE: DNA
<213> ORGANISM: Artificial Sequence
<220> FEATURE:
<223> OTHER INFORMATION: Description of Artificial Sequence: Synthetic
      promoter

<400> SEQUENCE: 19

```
agcttactcc ccatccccct gttgacaatt aatcatcggc tcgtataatg tgtggaattg   60
tgagcggata caatttcac acaggaaaca g                                   91
```

<210> SEQ ID NO 20
<211> LENGTH: 91
<212> TYPE: DNA
<213> ORGANISM: Artificial Sequence
<220> FEATURE:
<223> OTHER INFORMATION: Description of Artificial Sequence: Synthetic
      promoter

<400> SEQUENCE: 20

```
gatcctgttt cctgtgtgaa attgttatcc gctcacaatt ccacacatta tacgagccga   60
tgattaattg tcaacagggg gatggggagt a                                  91
```

<210> SEQ ID NO 21
<211> LENGTH: 63
<212> TYPE: DNA

```
<213> ORGANISM: Artificial Sequence
<220> FEATURE:
<223> OTHER INFORMATION: Description of Artificial Sequence: Synthetic
      oligonucleotide
<221> NAME/KEY: CDS
<222> LOCATION: (46)..(63)

<400> SEQUENCE: 21
aattgtgagc ggataacaat ttcacacagg aaacaggatc catat atg aag gaa gtg      57
                                                  Met Lys Glu Val
                                                    1 gag aac                                                                63
Glu Asn
      5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Lys Glu Val Glu Asn
  1               5
```

METHOD FOR PRODUCING THERAPEUTICALLY SUITABLE GLUTAMINASE

CROSS REFERENCE TO RELATED APPLICATION

This application is a divisional of U.S. application Ser. No. 08/050,482, filed Apr. 25, 1995, now U.S. Pat. No. 6,312,939 which is a national stage of PCT/US92/10421 filed Dec. 4, 1992.

TECHNICAL FIELD OF THE INVENTION

The present invention relates to a DNA coding for a therapeutically suitable glutaminase, a polypeptide which has the activity of a therapeutically suitable glutaminase, as well as their use in antiviral and anticancer therapy.

BACKGROUND OF THE INVENTION

Use of glutaminase to deplete glutamine in tumor-bearing hosts offers an attractive method for attacking cancer cells. Glutamine occupies an important role in the biosynthesis of a large number of cellular metabolites. Compared with normal tissues, some neoplasms have been shown to operate at a marginal level of glutamine availability because of decreased synthesis and stepped-up utilization (Levintow, 1954, *J. Natl. Cancer Inst.* 15:347–352; Roberts, et al., 1960, *Amino Acids, Proteins and Cancer Biochemistry* (J. T. Edsall, ed.), Academic Press, New York, N.Y. pp. 121–145; Weber, G., 1983., *Cancer Res.* 43:3466–3492; Sebolt, et al., 1984, *Life Sci.* 34:301–306). Experiments have revealed a negative correlation between glutamine content and the growth rate of transplanted rat hepatoma tumors. The in vivo concentration of glutamine in hepatoma 3924A was found to be 9-fold lower (0.5 mM) than in liver (4.5 mM) and lower than in any other rat tissues (2 to 5 mM) (Weber, 1983, *Cancer Res.* 43:3466–3492). In recent years accumulated data indicate that glutamine may be an important fuel source of cellular energy in a variety of neoplasms, including hematopoietic tumors, hepatomas, Ehrlich carcinoma, and HeLa cells (Abou-Khalil, et al., 1983, *Cancer Res.* 43:1990–1993; Kovacevic, et al., 1972, *J. Biol. Chem.* 33:326–333; Kovacevic, 1971, *Biochem. J.* 125:757–763; Reitzer, et al., 1979, *J. Biol. Chem.* 254:2669–2676).

L-asparaginase, the first enzyme to be intensively studied as an antitumor agent in man, is highly effective in the treatment of acute lymphoblastic leukemia. This enzyme, however, has little or no activity against any other neoplasms in humans. The enzyme glutaminase has activity against a much broader range of cancers than asparaginase.

Several mammalian and microbial glutaminase and glutaminase-asparaginase enzymes have been purified and characterized. Of these *Pseudomonas* 7A glutaminase-asparaginase appears to be best suited for therapeutic use because of its low $K_M$ for glutamine (micromolar range), good stability and activity in a physiological milieu, and long plasma half-life in tumor-bearing hosts (Roberts, 1976, *J. Biol. Chem.* 251:2119–2123, and Roberts, et al., 1979, *Cancer Treat. Rep.* 63:1045–1054).

The known mammalian glutaminase enzymes are not suitable for use as therapeutic agents because of their high $K_M$ values (millimolar range), and their requirement for phosphate esters or malate for activation. The *E. coli* glutaminases (A and B) are also unsuited for therapeutic use because of their high $K_M$ values (millimolar range), low activity at physiological pH (glutaminase A), or requirement for special activating substances (glutaminase B).

*Pseudomonas* 7A glutaminase-asparaginase is composed of four identical subunits with a molecular weight of approximately 35,000. Active enzyme sedimentation studies indicate that the catalytic activity is associated with the tetramer; no smaller active species are observed (Holcenberg, et al., 1976, *J. Biol. Chem.*, 251:5375–5380). The purified enzyme has a ratio of glutaminase to asparaginase activity of approximately 2:1. Binding studies with $C^{14}$-labelled analogs of glutamine (6-diazo-5-oxo-L-norleucine; DON) and asparagine (6-diazo-5-oxo-L-norvaline; DONV) suggest that the two analogs may react preferentially with hydroxyl groups at two different sites on the protein, and that the two binding sites act cooperatively as part of the active site (Holcenberg, et al., 1978., *Biochemistry* 17:411–417).

*Pseudomonas* 7A glutaminase-asparaginase was shown to have considerable antineoplastic activity against a variety of rodent leukemia (L1210, C1498, EARAD/1), ascites tumors (Taper liver, Ehrlich carcinoma, meth A sarcoma, S 180) and certain solid tumors (Walker 256 carcinosarcoma, B16 melanoma). Additionally, antagonism of glutamine by glutamine analogs and glutaminase was found to be strongly inhibitory to human colon, breast and lung carcinomas growing in athymic mice (McGregor, 1989, *Proc. Amer. Assoc. Cancer Res.* 30:578; Roberts, 1979, *Cancer Treat. Rep.* 63:1045–1054; Ovejera, 1979, *Cancer Res.* 39:3220–3224; Houchens, 1979, *Cancer Treat. Rep.* 63:473–476: Duvall, 1960, *Cancer Chemother. Rep.* 7:86–98).

An important characteristic of glutaminase therapy is that resistant strains do not develop after repeated treatments with this enzyme (Roberts, 1979, *Cancer Treat. Rep.* 63:1045–1054). Treatment with glutaminase was also shown to delay development of resistance against methotrexate (Roberts, 1979, *Cancer Treat. Rep.* 63:1045–1054).

A bioactive glutaminase-asparaginase has been shown to inhibit mouse retroviral disease. Glutamine depletion strongly inhibits the replication of Rauscher murine leukaemia retrovirus (RLV) in vitro. *Pseudomonas* 7A glutaminase-asparaginase (PGA), capable of depleting glutamine and asparagine for prolonged periods, was used to determine the therapeutic effectiveness, of glutamine depletion in mice infected with RLV or Friend virus. During PGA treatment of viremic animals, serum reverse transcriptase activity fell to control levels and infected animals did not develop splenomegaly. The therapeutic results obtained with PGA compare favorably with those of azidothymidine given intraperitoneally at 30 mg/kg/day (Roberts, 1991, *Journal of General Virology*, 72:299–305).

Despite the promise of glutaminase as a therapeutic agent, there are currently no therapeutically useful glutaminases available which can be produced cheaply and with little or no contamination by other substances, for example by endotoxins of a host microorganism. Moreover, a suitable enzyme is not available in quantities which are large enough to allow for wide-spread clinical trails.

SUMMARY OF THE INVENTION

It is an object of the invention to provide a method of inhibiting the replication of HIV in infected cells.

It is another object of the invention to provide a method of inhibiting the growth of Cancer cells.

It is yet another object of the invention to provide an *E. coli* cell which comprises a therapeutically suitable glutaminase.

It is still another object of the invention to provide a DNA molecule encoding a therapeutically suitable glutaminase.

It is an object of the invention to provide a therapeutically suitable glutaminase free of *Pseudomonas* endotoxin.

It is another object of the invention to provide methods of treating transformed cells in a body.

It is still another object of the invention to provide a therapeutic composition for treating neoplastic cells.

These and other objects of the invention are provided by one or more of the embodiments which are described below. In one embodiment a method of inhibiting the replication of HIV in HIV-infected cells is provided. The method comprises administering a therapeutically suitable glutaminase to HIV-infected cells in an amount sufficient to inhibit replication of HIV in said cells.

In another embodiment of the invention a method of inhibiting the growth of cancer cells is provided. The method comprises administering a bound complex to tumor cells which express a tumor-associated antigen, the amount of said complex administered being sufficient to inhibit DNA synthesis in said tumor cells. The complex comprises: (a) a therapeutically suitable glutaminase and (b) an antibody immunoreactive with a tumor associated antigen.

In yet another embodiment of the invention an *E. coli* cell is provided which comprises a *Pseudomonas* 7A glutaminase-asparaginase gene.

In still another embodiment of the invention an isolated and purified DNA molecule is provided. The molecule comprises a nucleotide sequence coding for a therapeutically suitable glutaminase.

In one embodiment of the invention a cell-free preparation of a therapeutically suitable glutaminase is provided. The preparation is free of *Pseudomonas* endotoxin.

In another embodiment of the invention a method of treating transformed cells in a body is provided. The method comprises: administering a plasmid comprising the nucleotide sequence of SEQ ID NO:1, said sequence under the transcriptional control of a tissue-specific promoter, said plasmid coated with poly-L-lysine covalently linked to a tissue-specific ligand.

In still another embodiment of the invention a therapeutic composition is provided. The composition comprises: a complex comprising a therapeutically suitable glutaminase and an antibody which is specific for a tumor-associated antibody.

In another embodiment of the invention a method of treating a tumor-bearing patient is provided. The method comprises the steps of: obtaining tumor infiltrating lymphocytes from a tumor-bearing patient; transfecting said tumor infiltrating lymphocytes with a vector which causes expression of *Pseudomonas* 7A glutaminase in human cells; and administering said transfected tumor infiltratina lymphocytes to the patient to supply said tumor with *Pseudomonas* 7A glutaminase.

In still another embodiment of the invention, a method of treating a tumor-bearing patient is provided which comprises the following steps: obtaining tumor infiltrating lymphocytes from a tumor-bearing patient; complexing said tumor infiltrating lymphocytes with a vector comprising the nucleotide sequence of SEQ ID NO:1, said vector causing expression of *Pseudomonas* 7A glutaminase in human cells; and administering said complex of lymphocytes and vector to the tumor-bearing patient to supply said tumor with *Pseudomonas* 7A glutaminase.

The present invention thus provides the art with new and useful anti-tumor and anti-viral therapeutic agents, as well as tools for making them and methods for using them.

The cloning and expression of the gene that encodes *Pseudomonas* 7A glutaminase-asparaginase in *E. coli* increases the glutaminase produced per liter of culture at least 12-fold, relative to the yield in *Pseudomonas* 7A. This markedly reduces the production cost of glutaminase and enables widespread clinical trials. Additionally, by producing the glutaminase in *E. coli* contamination of the antitumor drug by highly toxic *Pseudomonas* endotoxin is avoided.

BRIEF DESCRIPTION OF THE INVENTION

FIG. 1 shows the nucleotide and deduced amino acid sequence of the *Pseudomonas* 7A glutaminase gene. The top strand of the coding DNA sequence (SEQ ID NO: 1) is shown from 5'–3.' The numbers shown indicate nucleotide base pairs. The deduced peptide sequence is shown below the DNA sequence (SEQ ID NO: 2). The engineered N-terminal methionine residue is not shown.

FIGS. 2A and 2B depict the sequencing strategy for the *Pseudomonas* 7A glutaminase gene. FIG. 2A: Map of the P7A glutaminase showing selected restriction sites, the shaded area depicts the region encoding the actual gene product. Hatch marks represent 100 bp. Arrows below this figure show the approximate positions and orientations of sequencing primers with their accompanying names. The arrows with stops indicate the extent and direction of individual sequencing experiments. FIG. 2B: Names, sequences, and coordinates of sequencing primers are shown (SEQ IS NOS 3–11). Numbering is from the AAG encoding the N-terminal lysine residue.

Figure 4:
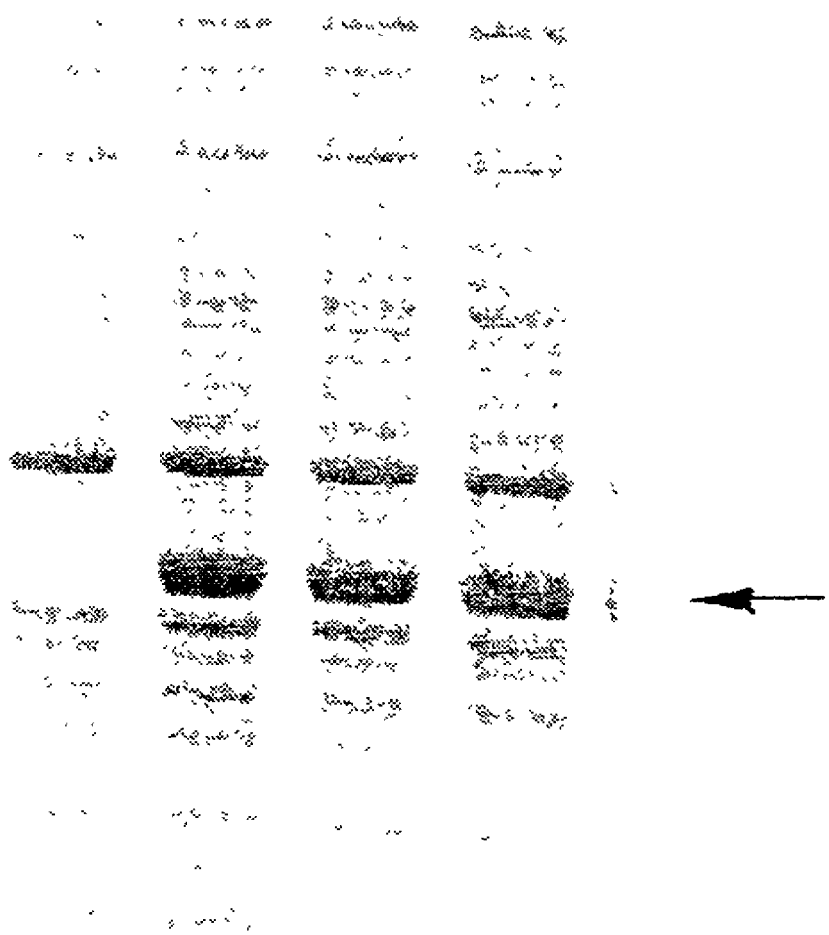

FIG. 4 shows denaturing polyacrylamide gel electrophoresis of crude extracts. Lane 1 shows an uninduced control and lanes 2–4 show inductions in whole cell extracts. The arrow indicates the position of the induced glutaminase band.

Figure 5:
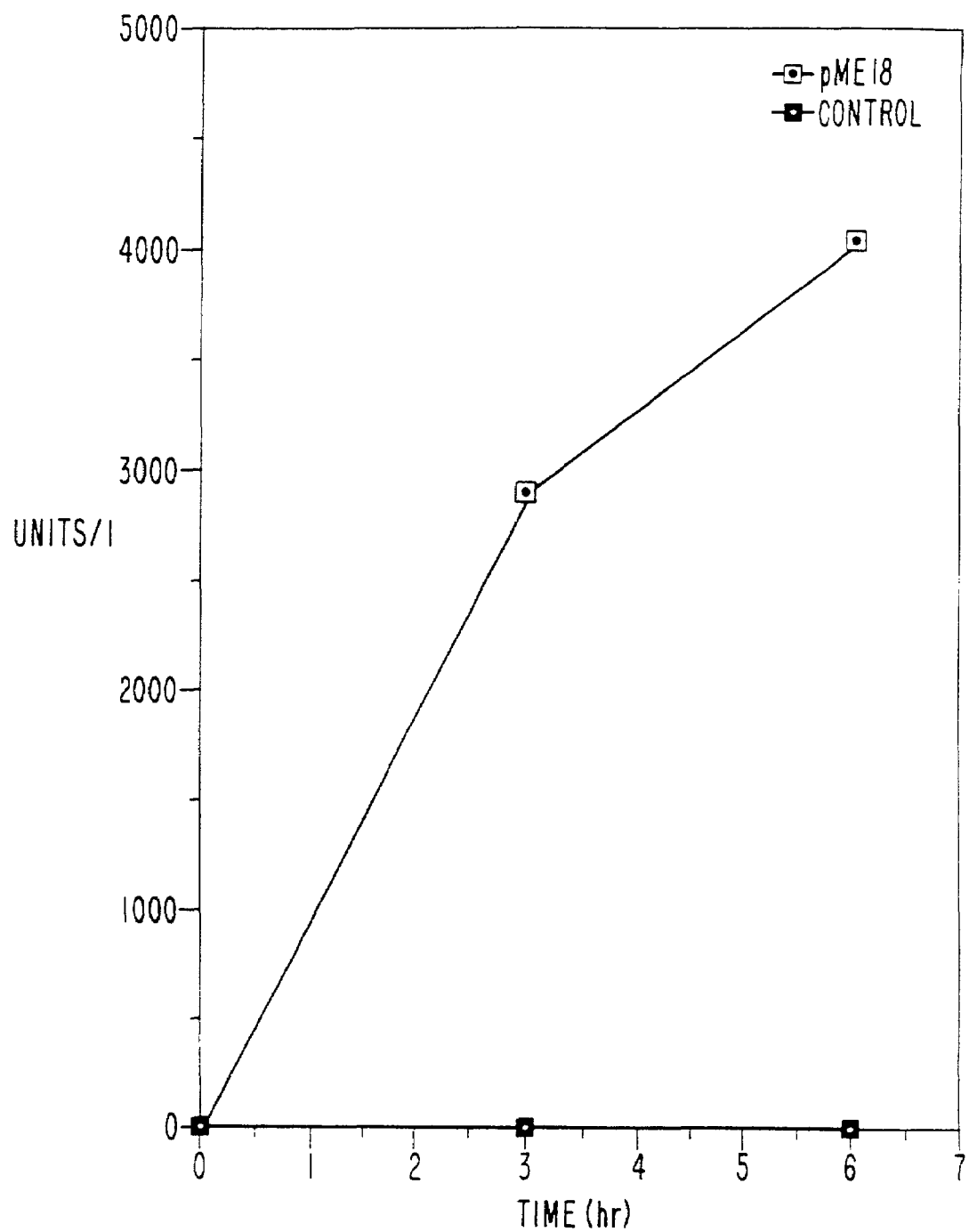

FIG. 5 depicts the induction by IPTG of PGA expression in *E. coli* containing pME18.

Figure 6:
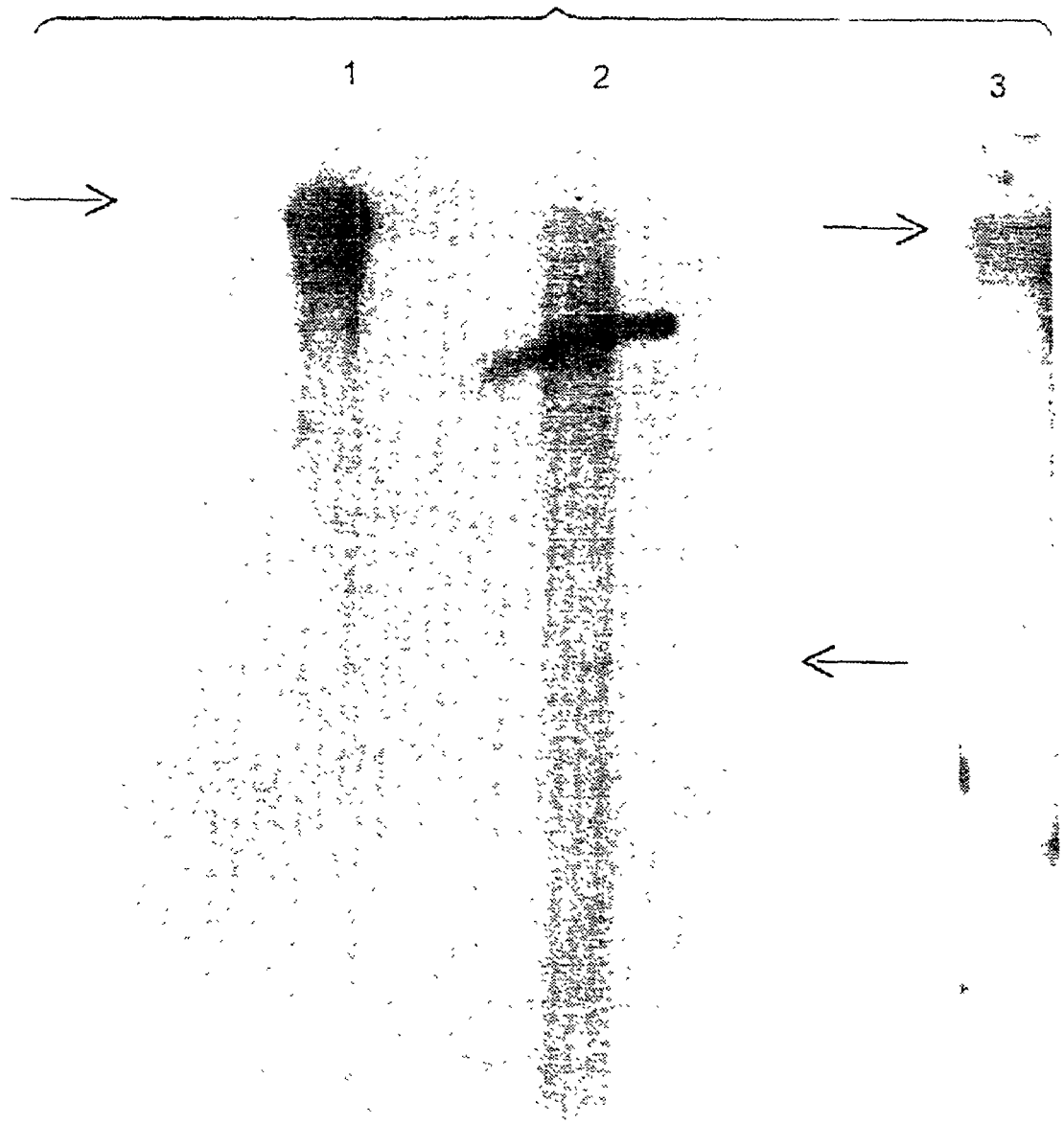

FIG. 6 shows hybridization of heterologous DNA to *Pseudomonas* 7A glutaminase sequences. Lane 1, *Pseudomonas* 7A; lane 2, *Pseudomonas aeruginosa*; lane 3, *Achromobacter sp.*

DETAILED DESCRIPTION OF THE INVENTION

It is a discovery of the present invention that glutaminase enzymes can be molecularly cloned in host organisms, despite the obstacle of host cell toxicity. Glutaminase activity must be strictly regulated in this process, because it is toxic to the host cells. Applicants have found that by means of a promoter which must be induced to express a downstream gene, as well as by using transcriptional terminators both 5' and 3' to the gene, that the glutaminase activity in the host cell can be controlled to a sufficient extent for the host cells to survive without loss of the DNA which encodes glutaminase. When the molecular clones are expressed in desirable host cells, glutaminase can be produced without contamination by endotoxins. It is a further finding of the present invention that glutaminase has inhibitory activity against human immunodeficiency virus (HIV) replication in infected cells. Moreover, it has been found that when glutaminase is complexed with anti-tumor antibodies and administered to tumor cells, that the growth of the tumor cells is inhibited to an extent far exceeding the inhibition by either glutaminase or antibody alone.

Glutaminase enzymes according to the present invention are therapeutically suitable if they display high enzyme activity at physiologic pH, i.e., between about pH 6.5 and 8.5. Therapeutically suitable glutarninase enzymes must have a low $K_M$, i.e., between $10^{-6}$ and $10^{-4}$ M. Additionally desirable properties of glutaminase enzymes for therapeutic use include:

1. High stability at physiologic pH.
2. Retains high activity and stability in animal and human sera and blood.
3. Cleared slowly from the circulation when injected into animals or humans. A plasma half-life ($t_{1/2}$) for glutaminase greater than six hours in mice and sixteen hours in humans is desirable.
4. Not strongly inhibited by the products of the reaction it catalyzes or by other constituents normally found in body fluids.
5. Does not require cofactors or prosthetic groups that can easily dissociate from the enzyme.
6. Narrow substrate specificity.
7. Effective irreversibility of the enzymatic reaction under physiologic conditions.
8. Available from an organism that contains low levels of endotoxin.
9. Low immunogenicity.

A number of amino acid-degrading enzymes that do not exhibit antitumor activity also fail to meet at least one of these criteria. For instance, E. coli glutaminase has a pH optimum of 5 and essentially no activity at physiologic pH. An ineffective form of E. coli asparaginase has a $K_M$ over 1 mM. Asparaginase enzymes from yeast, Bacillus coagulans, and Fusarium tricincrum all have excessively rapid clearance rates in mice.

The nucleotide sequence of one such therapeutically suitable glutaminases gene which was cloned is shown in SEQ ID NO:1. It is derived from the organism Pseudomonas 7A (P7A). The intact coding region encompasses 1008 base pairs and encodes a continuous polypeptide sequence of 336 amino acids (not including a 24 amino acid putative signal sequence). The C-terminus is punctuated by tandem stop codons and a putative transcriptional terminator.

The P7A glutaminase sequence which is disclosed here can be used to identify similar sequences encoding similar proteins. (See Watson, J. D. et al., in "Molecular Biology of the Gene." Benjamin/Cummings Publishing Company Inc., Menlo Park Calif., Vol. I, p. 608 (1987)). For example, Southern hybridization experiments can be carried out in which prokaryotic or eukaryotic organismal DNA is probed with all or part of the glutaminase gene of the present invention. Typically probes contain at least about 15 bases of the glutaminase sequence in order to ensure that other non-related sequences do not hybridize. Sufficiently high temperature and low salt concentrations further reduce hybridization to non-related sequences. Using such techniques, homologous genes have been found to dnaA of E. coli in Pseudomonas putida (Ingmer and Atlung, Mol. Gen. Genet. 232, 431 (1992)) and to ras in a variety of eukaryotic organisms (Matsui, Gene 76:313 (1989) and Hori, Gene 105:91 (1991)). There is a high probability that DNA sequences that hybridize to the P7A glutaminase DNA represent genes encoding enzymes of similar function. Genes which are isolated by this technique can be expressed, and the enzymes can be tested to determine if they share the desirable characteristics identified for the P7A glutaminase.

Probes contemplated by the present invention may be designed. as is known in the art, using the precise nucleotide sequences disclosed here for the P7A glutaminase gene, or based on the amino acid sequence of the enzyme. Thus for some purposes it may be desirable to employ degenerate probes, i.e., a mixture of probes whose sequences encode the same amino acids but contain different codons. Use of such probes should allow a broader range of homologous genes to be identified.

Using the DNA sequence of the P7A glutaminase (PGA), it is now possible to obtain other glutaminase genes from other organisms using complementation cloning. This is a technique which can be used even when there is no cross-hybridization or immunological cross-reactivity between two glutaminase genes or proteins. See Kranz, et al., Proc. Nail. Acad. Sci. 87:6629 (1990). Generally, the target organism is mutagenized and mutants are selected for an inability to utilize glutamine as a carbon and/or nitrogen source. Transformation with the P7A glutaminase should restore glutamine utilization in some of the selected mutants. These organisms should contain mutations in a gene homologous to PGA. Reversion of this mutant phenotype by introduction of DNA isolated from wild-type organisms can then be used as an assay to screen for the PGA homolog.

Provided the amino acid sequence of the glutaminase gene from P7A, as shown in SEQ ID NO:2, antibodies can routinely be obtained. These can be raised using peptide fragments or the complete protein as immunogens. The antibodies can be polyclonal or monoclonal, as is desired for the particular purpose. Antibodies can be used for screening strains for related enzymes. for quantitating the amount of enzyme present in a cell, and for detecting molecular clones from a library of clones.

The glutaminase genes according to the present invention can be readily modified to increase their compatibility with the host organism. For instance, codon usage varies from one organism to another. Therefore, it may be desirable in order to increase expression efficiency of the glutaminase, to alter the codons to conform to the codon usage pattern of the host. Such changes would not alter the amino acid sequence of the glutaminase but only the gene sequence. Such changes can be accomplished by any means known in the art, for example, oligonucleotide-directed mutagenesis can be used to introduce changes into a gene sequence. Alternatively, the entire gene can be synthesized.

Natural glutaminase contains a secretion signal, i.e., an N-terminal amino acid sequence of about 20 amino acids which is responsible for secretion through the cell membrane to the periplasmic space. Under some conditions, it may be beneficial to include a signal sequence in a glutaminase expression construct. The natural signal sequence may be used, or other signal sequences may be grafted onto the mature glutaminase sequence, to accomplish secretion of the enzyme. Use of a signal sequence may be advantageous for the expression of glutaminase, because it may diminish the toxic effect on the host cell. One signal sequence which may be used is the E. coli ompT signal. This signal, like others, is well known in the art. Secretion of glutaminase from the host cell may facilitate purification of the enzyme and should lead to the formation and recovery of authentic glutaminase.

Inducible promoters are desirable for expression of glutaminase because of the enzyme's inherent toxicity to living cells. Some inducible promoters which may be used are lac, tac, trp, mal, and $P_L$. Choice of a promoter is within the skill of the art.

Transcriptional terminators are also desirable both 5' and 3' to the glutaminase gene to prevent "read-through" expression. Many terminators are known and can be used. For a review see Watson, J. D. et al., in *Molecular Biology of the Gene*, Benjamin/Cummings Publishing Co., Menlo Park, Calif., Vol I, pp. 377–379 (1987). One terminator which Applicants have found useful is that of the T17 phage.

Modifications of the glutaminase gene were made for ease of production of enzyme in *E. coli*. In one such modified gene methionine is added at the N-terminus of the mature protein. In another such modified gene methionine, asparagine, and serine were added at the N-terminus of the mature protein. Neither of these additions destroyed enzyme activity or substrate specificity. Other similar changes are contemplated within the scope of the invention which do not significantly affect enzyme function.

According to the practice of the present invention it may be desirable to make modifications to the structure of glutaminase in order to improve its therapeutic properties or the ease of producing it. For example, it may be desirable to eliminate portions of the protein, by premature truncations or targeted deletions, to eliminate portions which are not essential for enzymatic function. A smaller protein may provide an improved therapeutic index by virtue of increased permeability into tumor masses, for example. Similarly, point mutations are also contemplated which may improve therapeutic or production characteristics. These may be achieved by directed or random mutagenesis, as is known in the art, or by thermocycle mutagenic amplification.

In addition, it may be desirable to produce chimeric proteins between glutaminase and other proteins. For example, it may be desirable to fuse genes encoding antitumor antibodies with the glutaminase gene of the present invention. As taught here, covalent complexes of these proteins can produce dramatic synergistic effects in the arresting of growth of tumor cells. It may provide production benefits to produce such complexes as a chimeric protein, rather than to post-translationally join the two proteins together in vitro. Fusing the glutaminase gene to other genes is also contemplated by the present invention, such as fusing to genes which encode tissue- or tumor-specific ligands, to facilitate direction of glutaminase to a desired region of the body.

The present invention offers the possibility of obtaining an asparaginase-free glutaminase which may have therapeutic advantages over glutaminase-asparaginase enzymes, since L-asparagine serves as a competitive inhibitor of glutamine degradation. Elimination of asparaginase activity from this enzyme may also reduce host toxicity. There are currently no therapeutically useful glutaminases available which lack asparaginase activity.

Inactivating the asparagine binding site of P7A glutaminase without affecting the glutamine binding site can be achieved, since binding studies with glutamine and asparagine analogues, DON and DONV, respectively, indicate that the glutamine and asparagine sites are not identical, though spatially they are close together. DON irreversibly binds the threonine at amino acid 20, whereas DONV appears to bind to a threonine or serine residue in a different region of the protein. The corresponding site-directed mutagenesis of the cloned DNA may be carried out according to standard techniques (Molecular Cloning, a laboratory manual—Sambrook et al.—Book 2, 2nd Ed., 1989, pp. 15.80–14.113, Site-directed Mutagenesis of Cloned DNA).

Through oligonucleotide and deletion mutagenesis, an enzyme that is exclusively glutaminase and that is sufficiently small to allow for improved penetrability of tumors and virus-infected tissue located in the extravascular space can be obtained. The DNA obtained according to Example 1 may be used. By analysis of the amino acid sequence (as deduced from the nucleotide sequence) and of X-ray crystallographic data, regions of the glutaminase protein that are not required for catalysis or structural integrity can be identified and can be deleted at the DNA level by deleting the relevant nucleotide sequences.

The glutaminase gene of the present invention can be used for transient gene therapy. Generally, the gene can be targeted to and taken up by transformed cells and expressed in those cells, so that the expressed glutaminase inhibits the growth of the transformed cells. This therapy has the benefit of avoiding the systemic exposure to the therapeutic agent, which may mitigate potential side-effects. In addition, if the cells are only transiently transfected, as is contemplated, the therapy is reversible.

One method which is contemplated for accomplishing this goal is the use of poly-L-lysine which has been modified with a tissue-specific ligand, as described by Wu et al. J. Biol. Chem. 266:14338–42 (1991). Examples of such tissue-specific ligands are galactose receptor of the liver, mannose receptor of macrophages, CD4 receptor of helper T cells, epidermal growth factor (EGF) receptor, and thyroid stimulating hormone (TSH) receptor. The glutaminase gene would be placed under the transcriptional control of a tissue-specific promoter. For example, the promoters from c-N-ras and c-myc could be used for expression in hepatic Rumors. These promoters are up-regulated in transformed cells, as compared to normal cells, and would therefore provide higher levels of expression in tumor cells than in normal cells. Plasmids are coated with the modified poly-L-lysine and injected into the bloodstream of the patient. The target cells will specifically take up the complexes due to the tissue-specific ligands. The target cells will specifically express the glutaminase construct due to the tissue-specific promoters. Since certain neoplasms have been shown to operate at a marginal level of glutamine availability, and the expression of glutaminase in these cells further depletes the glutamine pool in the tumor cells, the growth of these cells is specifically inhibited. Such a treatment should be useful against both fully transformed cells as well as cells in the early states of neoplasia, such as early stages of hepatitis B virus (HBV) infection. Since HBV activates expression of c-myc, it would also be expected to up-regulate this promoter in a glutaminase construct controlled by this promoter, leading to high level expression of glutaminase, which should kill the virus-infected cells.

Another technique for mediating uptake of the PGA gene by transformed or HIV-positive cells utilizes liposomes. (See Nicolau et al., *Methods in Enzymology*, vol. 149, pp. 157–176 (1987).) Cationic liposomes containing a vector able to express PGA are modified by the addition of specific receptor ligands or antibodies to the liposome bilayer. (See Hashimoto et al., *Methods in Enzymology*, vol. 121, pp. 817–829 (1986).) As with the polylysine method discussed above, liposomes have been used to successfully mediate the specific uptake of foreign DNA in vivo by liver cells through the galactose receptor.

Using the combination of cationic liposomes or polylysine as carriers of a PGA-expressing vector and tissue-specific reagents for targeting, glutaminase can be very specifically and transiently expressed in any tissue or cell of choice. Such tissue-specific reagents for targeting would include specific antibodies to surface markers and any manner of ligand for any specific cellular receptor. For example, the glutaminase gene can be specifically delivered to CD4+T cells (the type infected by HIV) in AIDS patients using a portion of the HIV coat protein that binds the CD4 antigen, as a ligand on a modified liposome. Carbohydrate modified liposomes containing a PGA expression system can also be used; the galactose receptor of liver, mediates the uptake of such modified liposomes. In addition to using ligands for receptors on the cell surface, antibodies to cell surface markers can be utilized in a similar manner to deliver these reagents to virtually any cell type.

An additional technique which can be useful in the treatment of patients with PGA is the use of carrier cells. (See Rosenberg, *Cancer Res.* (Suppl.). vol. 51, pp. 5074s–5079s (1991).) This technique takes advantage of the fact that certain T cells have the ability to infiltrate tumors (tumor infiltrating lymphocytes). These cells are taken from the cancer patient, transfected with a glutaminase expression vector, and returned to the patient. Upon return to the body and infiltration into the neoplasm, a high local level of glutaminase is provided. Alternatively, a bifunctional carrier can be utilized. Instead of transfection of the infiltrating lymphocytes with the PGA expression vector, the vector can be targeted to a specific surface marker on the lymphocytes as detailed above, for example using a monoclonal antibody in conjunction with poly-L-lysine. The presence of an additional targeting ligand (specific for the tumor cells) attached to the vector allows uptake of the PGA expression vector by the target tumor cells. Essentially, the infiltrating lymphocyte is used as a carrier to "drag" the expression vector to the tumor.

Administration of glutaminase to a body can be accomplished by any means known in the art. Glutaminase may be directed to particular organs or tissues by administration to arteries which feed the organs or tissues or by means of an organ or tissue-specific ligand. Direct conjugation of the PGA enzyme to functional targeting groups can be employed. These groups include antibodies, lectins, carbohydrates, hormones, peptides, or other compounds that can interact with cell surface molecules. For specific examples of this see *Methods in Enzymology*, vol. 112, pp. 238–306 (1985).

Glutaminase can be bound to antibodies, for example, those specific for tumor-associated antigens. A variety of techniques are known for complexing two proteins, any of which can be used with glutaminase, so long as enzyme activity and antibody binding capacity are not destroyed. Suitable techniques include those employing the heterobifunctional reagents SPDP (N-succinimidyl-3-(2-pyridyl dithio)propionate [Carlsson et al., *Biochemical Journal*, vol. 173, pp. 723–737 (1978)] or SMPT (4-succinimidyl-oxycarbonyl-α-methyl-α-(2-pyridyl dithio)toluene) [Thorpe et al. *Cancer Research*, vol. 47, pp. 5924–5931 (1987)]. A large number of antibodies have been described which are specifically reactive with tumor-associated antigens. Many are available from the American Type Culture Collection, 12301 Parklawn Drive, Rockville, Md. 20852, including those to breast, lung and melanoma tumor cells. For a review of tumor-specific antibodies see Foon, *Cancer Research*, vol. 49, pp. 1621–1631 (1989).

Tissue culture experiments with *Pseudomonas* 7A glutaminase (PGA) demonstrate that this enzyme strongly inhibits replication of human immunodeficiency virus (HIV) growing in the susceptible human T cell line H9. The presence of 0.4 μg PGA/ml culture medium caused virtually 100% inhibition of viral replication and 0.016 μg/ml caused 50% inhibition. A much greater concentration of PGA (50 μg/ml) was required to cause noticeable toxicity to the human H9 host cells. Although the tissue culture inhibition has been shown for HIV I-virus, other variant strains may also be inhibited.

These tissue culture results indicate that PGA is much more toxic to HIV than to the host human cells and it is expected that PGA will exhibit a high therapeutic index when administered to HIV-infected patients. Moreover, in combination with the glutamine antimetabolite DON, PGA proved to be particularly successful in the treatment of lung, breast or colon cancer. (McGregor, 1989, *Proc. Amer. Assoc. Cancer Res.* 30:587).

A DNA molecule which codes for a therapeutically suitable glutaminase and its corresponding polypeptide can be isolated from a microbial, animal or plant cell using oligonucleotide probes prepared according to known glutaminase protein sequences. Preferably, the DNA is isolated from *Pseudomonas* 7A cells.

EXAMPLE 1

This example demonstrates the identification of a clone containing the sequence coding for *Pseudomonas* 7A glutaminase and determination of its nucleotide sequence.

The glutaminase product is an enzyme that degrades glutamine (an amino acid that participates in more metabolic processes than any other amino acid) and therefore hinders growth. In more than two dozen independent experiments, we had been unable to clone the glutaminase in a variety of contexts. We have found it unclonable in high copy number backgrounds such as pUC. It also proved refractory to cloning in the absence of an upstream transcriptional terminator and a very tightly regulated promoter.

Chromosomal DNA was isolated from *Pseudomonas* 7A (a soil isolate organism, which has been deposited with the American Type Culture Collection under deposition number ATCC 29598) essentially as described (Strom, 1986, *J. Bacteriol.* 165:367–372), and was partially digested with the restriction enzyme Sau3A. Fragments of this digest averaging 5–10 kb were isolated by preparative agarose gel electrophoresis, and cloned into the BamHI site of the vector pBR322. The resultant genomic library (in *E. coli* strain LE392, ATCC accession no. 33572) was screened using mixed oligonucleotide probes (Wallace, et al., 1981, *Nucleic Acids Res.* 9:879–89, and Paddock, G. V., 1987, *Biotechniques* 5:13–16). Partial peptide sequence information was obtained and used to deduce the three oligonucleotide probes shown in Table 1. Oligonucleotide probes were selected for peptide sequence information from the amino terminus of the enzyme (probe A), from the carboxyl terminus (probe C), and from a peptide near the middle of the protein (probe B). Probe B was selected for the initial screening of 3560 ampicillin-resistant transformants. From the initial screening two hybridization positive clones were identified. These were rescreened using probes A and C. Both clones hybridized to probe A, but only one of the clones, pME0.5, hybridized -with probe C. Because pME.0.5 had hybridized with all three probes, it was selected for further analysis.

Crude cell extracts of strain LE392 transformed with plasmid pME0.5 were prepared by breaking aliquots of an overnight culture, and centrifuging the homogenate at 15,000 rpm to remove unbroken cells and cell debris. The resulting supernatant was assayed for glutaminase activity by direct Nesslerization of ammonia (Roberts, J., 1976, *J. Biol. Chem.* 251:2119–2123). To minimize interfering activity by either of the *E. coli* glutaminase enzymes, the enzyme assay was carried out at pH8.0 and utilizing D-glutamine as the substrate. Neither *E. coli* enzyme is active under these conditions, while the *Pseudomonas* 7A glutaminase (PGA)

retains 87% of its activity (Pruisner, 1976, *J. Biol. Chem.*, 251:3447–3456 and J. Roberts, 1976, *J. Biol. Chem.* 251: 2119–2123). Control experiments with crude cell extracts confirmed the efficacy of this assay to measure PGA activity in the absence of *E. coli* glutaminase activity. No activity was found.

TABLE 1

OLIGONUCLEOTIDE PROBES USED FOR DETECTING THE GLUTAMINASE GENE

Peptide Sequence NH$_2$-Lys-Glu-Val-Glu-Asn
(1–5) of
Sequence
SEQ ID NO: 2

Probe A          AA (AG) GA (AG) GT (TCAG) GA (AG) AA
(SEQ ID NO: 2)
(14-mer × 32)

Peptide Sequence Met-Asn-Asp-Glu-Ile-Gln
(161–166) of
SEQ ID NO: 2

Probe B          ATGGA (TC) GA (TC) GA (AG) AT (TCA) GA (AG)
(SEQ ID NO: 13)
(18-mer × 48)

Peptide Sequence Ile-Phe-Trp-Glu-Tyr-COOH
(332–336) of
SEQ ID NO: 2

Probe C          AT (TCA) TT (TC) TGGGA (AG) TA
(SEQ ID NO: 14)
(14-mer × 12)

In order to confirm the identity of the putative PGA clone, the region of homology to the probes used for screening was localized by Southern blot analysis, and the appropriate fragments were partially sequenced. This analysis identified a 1.1 Kb SalI fragment which hybridized to probe A, and a 1.5 Kb SalI fragment which hybridized to probe B. This indicated that there was a SalI site within the gene, and that sequencing from this site would immediately confirm the identity of the gene as PGA by comparing the nucleotide sequence with the known amino acid sequence. Sequencing of the 1.1 kb SalI fragment showed that this fragment encodes the N-terminal 42 amino acids of the glutaminase.

For convenient sequencing, various fragments of the glutaminase coding region were sub-cloned into a ColE1-based plasmid using standard protocols Sambrook, et al., supra. These include the 1.1 kb N-terminal SalI fragment (pME1), the 1.5 kb C-terminal SalI fragment (pME2), the thermocyle amplification-mutagenized N-terminus (pME3), and the 200 bp C-terminal PstI fragment (pME11). Numerous sequencing primers were synthesized using pre-determined glutaminase DNA sequences (see FIG. 1).

Using both the full-length clone, pME0.5, and the sub-cloned gene fragments, the glutaminase gene was sequenced in both directions by Sanger's chain-termination DNA sequencing method. *Proc. Natl. Acad. Sci. USA* 74:5963 (1977). The purified double-stranded templates were denatured by the standard alkaline-denaturation method.

The intact coding region (SEQ ID NO:1) encompasses 1008 base pairs and encodes a continuous peptide sequence of 336 amino acids (not including a 24 amino acid putative signal sequence). The C-terminus is punctuated by tandem stop codons and a putative transcriptional terminator. Based on matching this sequence information with the peptide sequencing data, it was concluded that the PGA gene had indeed been cloned.

EXAMPLE 2

This example demonstrates the expression of the gene for *Pseudomonas* 7A glutaminase.

Figure 2A:
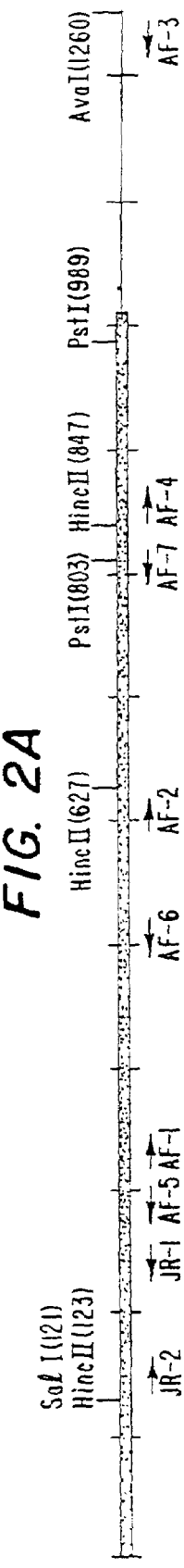
Figure 2B:
Figure 3A:
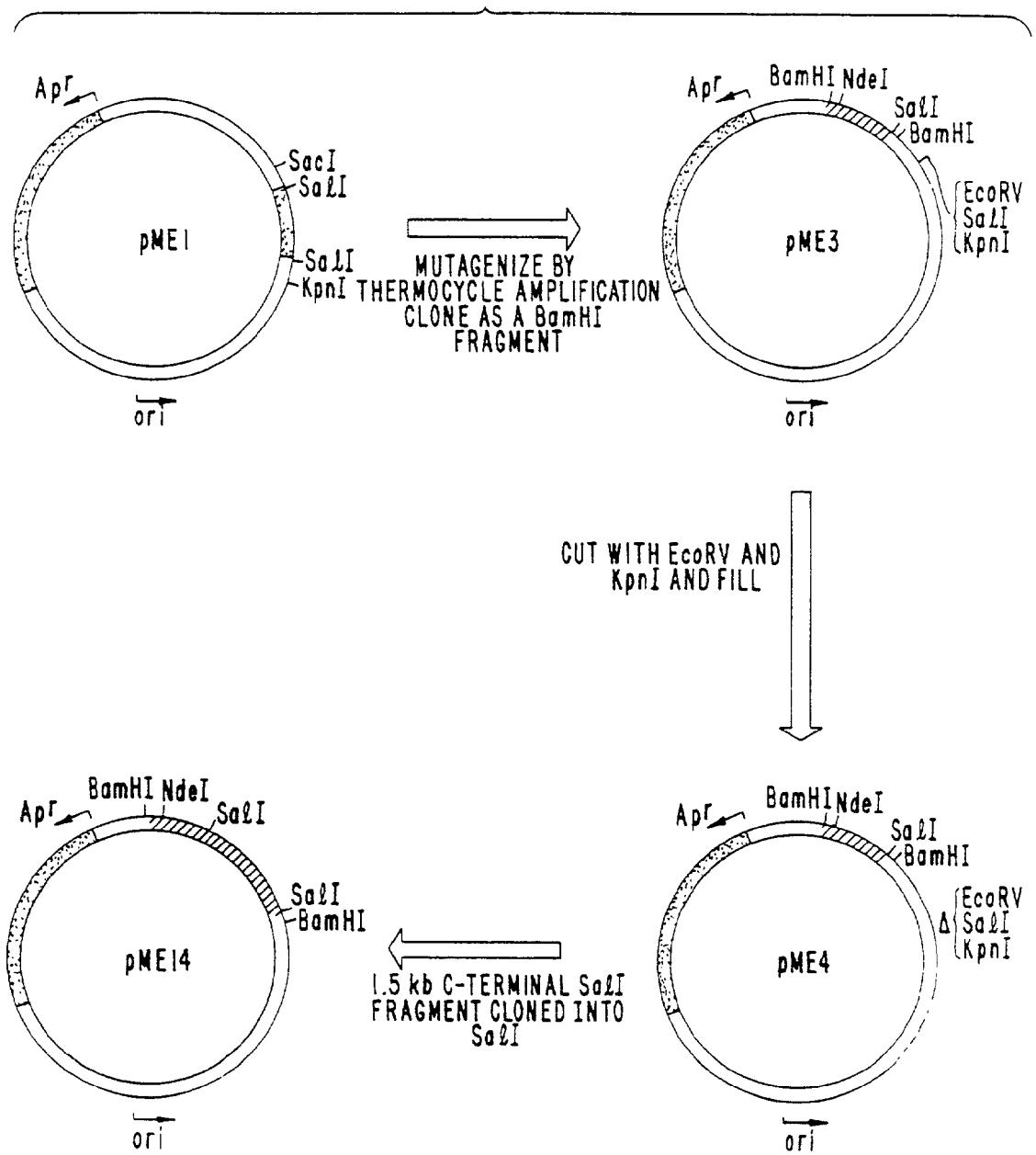
FIG. 3A depicts recombinant constructs with P7A glutaminase. "Ap'" is a β-lactamase gene, conferring ampicillin resistance. "T" represents a transcriptional terminator. "Ptac" is the promoter. "ori" is the pBR322 origin of replication.
Figure 3B:
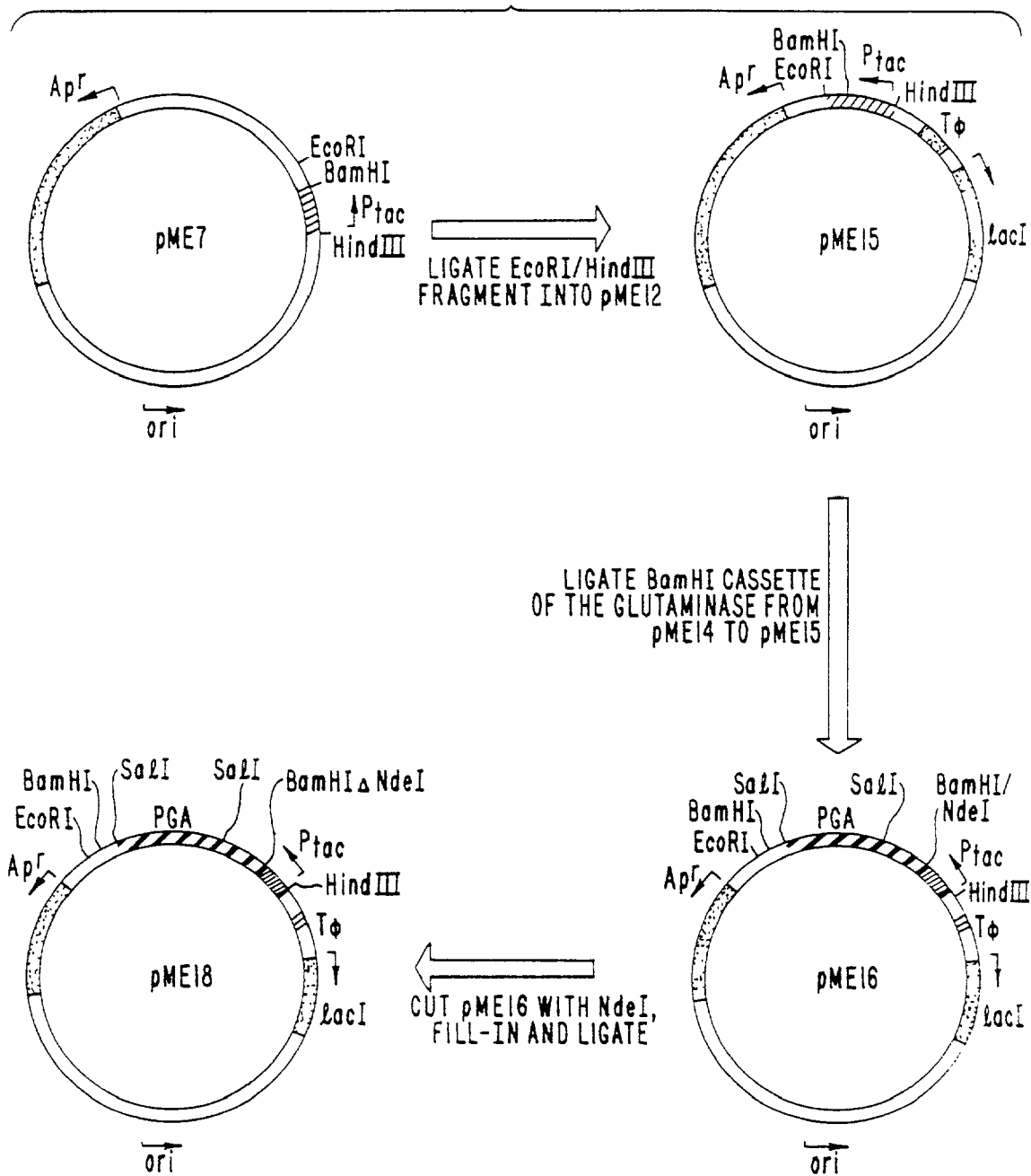
FIG. 3B shows the construction of a P7A glutaminase over-expressing plasmid.

Initial experiments showed that even among strong, regulated promoters (e.g. $\lambda P_L$)PGA was refractory to overproduction. In order to obtain high level controlled expression of the Psuedomonas 7A (P7A) glutaminase in *Escherichia coli*, we first designed a new vector, pME15 (see FIGS. 3A and 3B for cloning, and Table 2). The backbone of the vector was pME12 (see Table 2) and contains the following features: β-lactamase gene (conferring ampicillin resistance), lac I (repressor of the lactose operon), a T7 transcriptional terminator, and a low copy-number ColE1-type origin of replication (pBR322-derived).

TABLE 2

Plasmids Used in Construction of a High-Level Expression Plasmid

| | |
|---|---|
| pME0.5 | genomic clone from a library of Sau3A fragments of P7A chromosomal DNA cloned into the BamHI site of pBR322. This clone contains the full-length glutaminase gene. |
| pME1 | the N-terminal 1.1 kb SalI fragment of pME0.5 cloned into the SalI site of a ColE1-based plasmid. |
| pME2 | the C-terminal 1.5 kb SalI fragment of pME0.5 cloned into the SalI site of a ColE1-based plasmid. |
| pME3 | the thermocycle amplification mutagenized front end of the P7A glutaminase containing a BamHI site and an NdeI site at the N-terminus and a BamHI site after the first SalI site cloned into a ColE1-based plasmid. |
| pME4 | pME3 cut with EcoRV and KpnI, flushed with T4 DNA Polymerase and re-ligated. This deletes the SalI site in the polylinker, leaving the SalI internal to the glutaminase as unique. |

TABLE 2-continued

Plasmids Used in Construction of a High-Level Expression Plasmid

| | |
|---|---|
| pME7 | The 90 bp HinDIII/BamHI Ptac-containing fragment resulting from the ligation of overlapping oligonucleotides (Table 3) cloned into pUC19. |
| pME11 | The 200 bp PstI fragment from pME2 which flanks the stop codon of the P7A glutaminase was cloned into the PstI site of a ColE1-based plasmid. |
| pME12 | pBR322 with the *E. coli* lacI gene within the tet gene at the SalI site and the T7 transcriptional terminator at the BamHI site. |
| pME14 | the 1.5 kb SalI fragment from pME2 was cloned into pME4, reconstituting the full-length glutaminase gene. |
| pME15 | The HinDIII/EcoRI fragment from pME7 (containing Ptac) was cloned into pME12. |
| pME16 | The BamHI cassette of pME14 containing the glutaminase gene was cloned into the BamHI site of pME15. This should give the tac promoter driving glutaminase expression. |
| pME18 | pME16 was opened at the unique NdeI site at the N-terminus of the glutaminase and filled in with the Klenow fragment of *E. coli* DNA Polymerase I. This blunt-end product was re-ligated, yielding a distance of 9 bases between the Shine-Dalgarno sequence and the glutaminase start codon. This should give optimal levels of expression. | and will therefore not interfere with plasmid propagation. A transcriptional terminator is present immediately upstream of the transcriptional start site, eliminating "read-through" transcription. The combination of control by lac I and an upstream transcriptional terminator provides a vector with the ability to stably propagate and express even the toxic glutaminase genes. Additionally, having a plasmid-encoded lac I gene also allows for virtual host independence.

As we have previously observed, the full length P7A glutaminase is present on two SalI fragments: a 1.1 kb fragment containing the N-terminus of the gene and a 1.5 kb fragment containing the C-terminus. In order to clone this gene into an expression system, we wished to engineer the sequence at the N-terminus to provide convenient sites for restriction endonuclease. This would allow the cloning of the gene into numerous established expression vectors in addition to our vector, pME15. For this reason, we used mutagenic thermocycle amplification primers (see Table 3) to generate a BamHI site and an NdeI site at the N-terminal lysine residue. This mutagenesis also adds a methionine residue immediately upstream of the N-terminal lysine. We also added a BamHI site after the internal SalI site.

TABLE 3

Oligonucleotides Used in Construction
of a High Level Expression Plasmid

```
Primers for thermocycle amplification mutagenesis of the glutaminase:
N-terminus (SEQ ID NO: 15)
        GCCGGATCCA TATGAAGGAA GTGGAGAACC AGCAG Internal SalI site (SEQ ID NO: 16)
        GCGCGGATCC GTCGACGCCA ACCTTGGCAG Mutagenized N-terminus of the glutaminase (SEQ ID NOS: 17 & 18)
        GGATCCAT ATG AAG GAA GTG GAG AAC
                Met Lys Glu Val Glu Asn. . .

Oligonucleotides for tac promoter
     top (SEQ ID NO: 19):
        AGCTTACTCC CCATCCCCCT GTTGACAATT AATCATCGGC TC
        GTATAATGTG TGGAATTGTG AGCGGATAAC ATTTCACAC AGGAAACAG Bottom (SEQ ID NO: 20):
        GATCCTGTTT CCTGTGTGAA ATTGTTATCC GCTCACAATT CCACACA
        TTATACGAGC CGATGATTAA TTGTCAACAG GGGGATGGG AGTA Filled in product of pME18 (SEQ ID NO: 21 & 22)
                  lacO                    S.D.         S.D.
        5'     AATTGTGAGCGGATAACAATTTCACAC    AGGA    AAC    AGGATCCATAT ATG    AAG
                                                                        Met    Lys

GAA        GTA        GAG        AAC 3'

GLU        Val        Glu        Asn . . .
```

We chose as our promoter the tac (hybrid trp/lac) promoter containing a lac operator sequence (conferring susceptibility to repression by lac I). (deBoer, et al., *Proc. Natl. Acad. Sci. USA,* 80:21 (1983), and Russel, et al., *Gene* 20:231 (1982).) We synthesized overlapping oligonucleotides which were ligated and cloned as a BamHI/HindIII fragment into the cloning vector pUC19, resulting in pME7. The BamHI/EcoRI fragment of pME7 was cloned into pME12 to form pME15. This provides the tac promoter controlled by lac I and hence, it is inducible with isopropyl-β-thio-D-galactoside (IPTG). This promoter is active in the same orientation as the unidirectional origin of replication The thermocycle amplification-mutagenized N-terminal fragment of the glutaminase gene was cloned into a ColE1-based vector as a BamHI fragment (pME3). The polylinker between KpnI and EcoRV was deleted removing the endogenous SalI site, generating pME4. The full-length glutaminase was reconstituted by ligation of the 1.5 kb SalI fragment, encoding the C-terminus, into the unique SalI site of pME4, yielding pME14. The 1.7 kb BamHI fragment from pME14 was cloned into the expression vector pME15. This clone (pME16) provides glutaminase expression driven by the tac promoter. In an attempt to achieve higher levels of expression, we opened pME16 at the NdeI site and filled it in using the Klenow fragment of *E. coli* DNA Polymerase I. Upon re-ligation, the spacing between the Shine-Dalgarno sequence and the translation start-site became optimal (see Table 3).

This vector (pME18) is stable and directs expression of authentic P7A glutaminase. It has been deposited at the American Type Culture Collection under the terms of the Budapest Treaty on Nov. 3, 1992, and assigned the accession no. 69117. For the purpose of protein production, cells were grown to mid-log phase at 37° C. and treated with 0.4 mM IPTG for 1–6 hours. Protein production was monitored by denaturing polyacrylamide gel electrophoresis (FIG. 4) and glutaminase specific activity. Such culturing has yielded activities as high as 4100 U/liter of culture, representing approximately 3% of the total cellular protein. Since *Pseudomonas* P7A produces only 350 U/liter, this represents a 12-fold increase in enzyme production.

In order to assure that the observed activity was contributed by the *Pseudomonas* glutaminase as opposed to endogenous *E. coli* glutaminase A and B, the reaction was repeated with D-glutamine at pH 8. Only *Pseudomonas* enzyme functions under these conditions; in fact, it converts D-glutamine to glutamate 87% as efficiently as it converts L-glutamine. The results demonstrate that all the measurable activity was contributed by PGA. Bradford protein assays were also done on the crude cell extracts to allow calculation of the enzyme, activity as specific activity. Samples of each extract were also analyzed on SDS-PAGE gels essentially as described by Laemmli (Laemmli, U.K. (1970) Nature (London) 227:680–685). The resulting enzyme induction curve is shown in FIG. 5, where the increase in glutaminase activity in the cell extract using D-glutamine as substrate is shown. As can be seen, the activity of the enzyme utilizing D-glutamine as a substrate increases over 4000-fold after IPTG induction, while control culture shows virtually no increase in D-glutaminase activity.

For the sake of efficient translation of the glutaminase in *E. coli*, an N-terminal methionine codon was added (see Table 3). It was of some concern whether or not this extra amino acid would alter the activity of the enzyme. To test this, we measured enzyme activity against L- and D-glutamine as well as L- and D-asparagine. The ratios of activity between the L- and D-isomers were the same for both the native and the engineered enzyme (e.g., L-:D-glutamine and L-:D-asparagine). Another concern was that this alteration might adversely effect the in vivo half-life. To test this, we performed in vivo half-life studies in mice; both enzymes showed the same in vivo half-life. Based on these combined data, we conclude that the extra N-terminal methionine residue does not alter the biological activity of the enzyme.

EXAMPLE 3

This example demonstrates the use of P7A glutaminase sequences to identify homologous sequences in other bacterial species.

Chromosomal DNA from *Pseudomonas aeruginosa* and *Achromobacter sp.* was isolated using standard protocols. After complete digestion with EcoRI, DNA fragments were resolved on a 30 cm, 1% agarose gel at 50V for 15 hours in 89 mM Tris-Cl, pH8; 89 mM Borate; and 1 mM EDTA. Transfer and hybridization were as described (Maniatis et al. *Molecular cloning: A laboratory Manual*, pp. 382–389, Cold Spring Harbor Laboratory, Cold Spring Harbor, N.Y. 1982) using stringent conditions. The probe was the coding region of the P7A glutaminase gene labeled with $\alpha$-$^{32}$P deoxycytosine triphosphate. Lane 1, *Pseudomonas* 7A (2 hr. exposure); lane 2, *Pseudomonas aeruginosa* (6 hr. exposure); lane 3, *Achromobacter sp.* (24 hr. exposure). Results are shown in FIG. 6.

EXAMPLE 4

This example demonstrates in vitro inhibition of human melanoma cells by glutaminase linked to anti-melanoma antibody.

Human melanoma cells (Heatherington) were incubated in vitro for 30 minutes with either free R24 anti-melanoma antibody, free glutaminase, or covalently bound antibody-glutaminase complex. The covalently bound antibody-glutaminase complex was prepared utilizing the heterobifunctional reagent SPDP (N-succinimidyl-3-(2-pyridyl dithio)propionate [Carlsson et al., *Biochemical Journal*, vol. 173, pp. 723-$^{7}$37 (1978)]. The cells were washed and placed in fresh tissue culture media, and $^3$H-Thymidine incorporation was measured. The incorporation of the melanoma cells is shown in Table 4. Neither free antibody or free glutaminase inhibited thymidine incorporation. Only cells incubated with the antibody-glutaminase complex exhibited inhibition of $^3$H-Thymidine incorporation. Thus, the two components, antibody and glutaminase act synergistically to inhibit tumor cell growth.

TABLE 4

| TREATMENT | % INHIBITION OF $^3$H-THYMIDINE INCORPORATION |
| --- | --- |
| Free Antibody | 0 |
| Free Glutaminase (0.06 IU/ml) | 0 |
| Antibody-Glutaminase (0.06 IU/ml) Complex | 93 |

We claim:

1. A method of producing a therapeutically suitable glutaminase comprising:
    culturing a recombinant microorganism which comprises a heterologous nucleotide sequence that codes for a therapeutically suitable glutaminase; and
    collecting said therapeutically suitable glutaminase produced by said microorganism, wherein said nucleotide sequence encodes the protein of SEQ ID NO: 2.

2. A method according to claim 1, wherein said microorganism is a bacterium.

3. A method according to claim 2, wherein said microorganism is *E. coli*.

4. A method according to claim 1, wherein said protein is encoded by the nucleotide sequence of SEQ ID NO: 1.

5. A method according to claim 1 wherein the protein encoded by the nucleotide sequence has a $K_m$ of $10^{-6}$ to $10^{-4}$ M for its reactants and remains active in human sera.

6. A method according to claim 1, wherein said glutaminase is a *Pseudomonas* glutaminase.

* * * * *